United States Patent [19]

Clark et al.

[11] Patent Number: 5,073,192
[45] Date of Patent: Dec. 17, 1991

[54] DIPHENYL ETHER HERBICIDES

[75] Inventors: Michael T. Clark; Ian J. Gilmore, both of Sittingbourne, England

[73] Assignee: Shell Internationale Research Maatschappij B.V., The Hague, Netherlands

[21] Appl. No.: 592,517

[22] Filed: Oct. 2, 1990

Related U.S. Application Data

[63] Continuation of Ser. No. 230,099, Aug. 9, 1988, abandoned.

[30] Foreign Application Priority Data

Sep. 1, 1987 [GB] United Kingdom ............... 8720509

[51] Int. Cl.$^5$ ............................................. A01N 43/08
[52] U.S. Cl. ..................................... 71/88; 549/307; 549/466
[58] Field of Search ..................... 71/88; 549/307, 466

[56] References Cited

U.S. PATENT DOCUMENTS 4,334,915 6/1982 Hiraga et al. .................... 71/108

FOREIGN PATENT DOCUMENTS 145078 6/1985 European Pat. Off. .
219144 4/1987 European Pat. Off. .
2182328 5/1987 United Kingdom .

OTHER PUBLICATIONS

Clark et al., CA 109:68854f.
C.A. 80:59757q (1974).
C.A. 73:98664z (1970).
Relles, H. M. et al., J. Org. Chem. 45, 1374–1379 (1980).
Williams, F. J. et al., J. Org. Chem. 42, No. 21, 3414–3419 (1977).
Williams, F. J. et al., J. Org. Chem. 42, No. 21, 3425–3431 (1977).

*Primary Examiner*—Jane T. Fan

[57] ABSTRACT

Phenoxy phthalide derivatives having the general formula II:

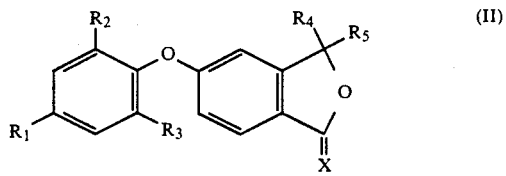

wherein $R_1$ represents a hydrogen or halogen atom or an alkyl or haloalkyl group; $R_2$ and $R_3$, which may be the same or different, each independently represents a hydrogen or halogen atom or an alkyl, haloalkyl, nitro or cyano group; $R_4$ represents a saturated alkyl group; $R_5$ represents an unsaturated alkyl group; and X represents an oxygen or sulphur atom, are useful as herbicides.

13 Claims, No Drawings

DIPHENYL ETHER HERBICIDES

This application is a continuation of application Ser. No. 07/230,099, filed Aug. 9, 1988, now abandoned.

This invention relates to certain diphenyl ether derivatives and their preparation, herbicidal compositions containing the compounds, and their use in combating undesired plant growth.

The applicants' European Patent Application No. 145078 describes and claims a herbicidal composition which comprises a carrier and, as active ingredient, a diphenyl ether derivative having the general formula I:

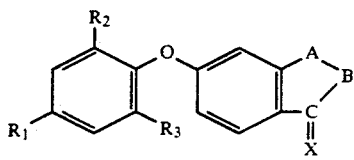

wherein $R_1$ represents a hydrogen or halogen atom or an alkyl or haloalkyl group; $R_2$ and $R_3$, which may be the same or different, each independently represents a hydrogen or halogen atom or an alkyl, haloalkyl, nitro or cyano group; and B and A, inter alia, represent, respectively, an oxygen atom and a group of formula $=C(R_4)_2$ in which each $R_4$, which may be the same or different, represents a hydrogen or halogen atom or an optionally substituted alkyl, cycloalkyl, alkenyl, alkynyl, aryl, aralkyl, alkaryl, alkoxy, cycloalkoxy, alkenyloxy, alkynyloxy, alkoxycarbonylalkoxy, alkylthio, acyl, acyloxy, carboxyl, alkoxycarbonyl or heterocyclic group, an amino group of formula $NR_6R_7$, or when one $R_4$ represents a hydrogen atom, an alkoxy group or a hydrocarbon group, then the other may represent a hydroxyl group, or both groups $R_4$ together may represent an imino group of formula $=NR_6$;

$R_6$ and $R_7$, which may be the same or different, each represents a hydrogen atom or an optionally substituted alkyl, aryl or acyl group; and X represents an oxygen or sulphur atom.

It has now been unexpectedly found, that a certain group of the compounds broadly described in EPA 145078, but not specifically disclosed therein, possesses significantly higher selectivity in cereal crops than a representative diphenyl ether phthalide actually disclosed in EPA 145078.

Accordingly, the present invention provides phenoxy phthalide derivatives having the general formula II:

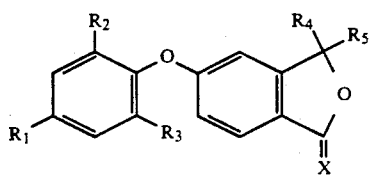

wherein $R_1$ represents a hydrogen or halogen atom, preferably chlorine, or an alkyl or haloalkyl group, suitably of 1-4 carbon atoms, preferably trifluoromethyl; $R_2$ and $R_3$, which may be the same or different, each independently represents a hydrogen or halogen atom, preferably chlorine, or an alkyl or haloalkyl group, suitably of 1-4 carbon atoms, for example trifluoromethyl, or a nitro or cyano group; $R_4$ represents a saturated alkyl group; $R_5$ represents an alkenyl or alkynyl group; and X represents an oxygen or sulphur atom.

Preferred compounds are those wherein $R_1$ represents a halogen atom, more particularly chlorine, or, especially, a trifluoromethyl group; $R_2$ represents a nitro, cyano, trifluoromethyl or, especially, a halogen atom, more particularly chlorine; and $R_3$ represents a halogen, more particularly chlorine, or, especially, a hydrogen atom.

The groups $R_4$ and $R_5$ are preferably groups of 1-5 carbon atoms. Preferably $R_4$ is a methyl or ethyl group. Preferably $R_5$ is a vinyl or ethynyl group.

It will be appreciated that the compounds of the invention can exhibit stereoisomerism and the invention is intended to include stereospecific enantiomers of the compounds of formula II.

The invention also provides a process for the preparation of a phenoxy phthalide derivative of formula II as defined above which comprises reacting a compound of formula III

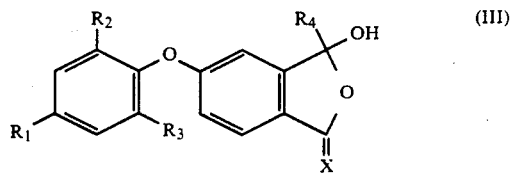

where $R_1$, $R_2$, $R_3$, $R_4$ and X are as defined above, with an organometallic compound of formula $R^5$—M—Hal (IV), where $R^5$ is as defined above, M represents a metal atom and Hal represents a halogen atom.

The moiety Hal is preferably a bromine or iodine atom.

The organometallic reagent used is preferably an organomagnesium compound (Grignard reagent), which may be prepared according to established procedures, e.g. by taking up the appropriate alkenyl or alkynyl halide and magnesium metal in an aliphatic ether, such as diethyl ether, in the absence of water, or may be prepared by passing the alkene or alkyne gas through a solution of an alkyl Grignard reagent. The reaction of the compound of formula III with that Grignard reagent is suitably carried out in a solvent, which may also be diethyl ether, or may be a different inert organic solvent such as tetrahydrofuran. The formation of the Grignard reagent and its reaction with the compound of formula III are each suitably carried out in the temperature range 0° to 50° C., preferably at ambient temperature. The Grignard organomagnesium complex may be supplemented by the generation of an organocadmium complex through the addition of cadmium chloride.

Alternatively, compounds of formula II where $R^5$ is an alkynyl group may be prepared by reacting a compound of formula III as defined above with a compound of formula $R^5M$ where M is an alkali metal. Examples of compounds of formula $R^5M$ are lithium and sodium acetylides.

Compounds of formula III may conveniently be prepared by alkaline hydrolysis of a compound of formula V

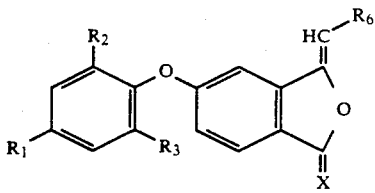

where $R_1$, $R_2$, $R_3$ and X are as defined above and $R_6$ represents hydrogen or a saturated alkyl group, preferably having 1 to 4 carbon atoms, preferably methyl, in accordance with the process described in our copending U.K. Application No. 8720511.

Compounds of formula V may conveniently be prepared from the corresponding phthalic anhydride by reaction with a compound of formula $R_6CH_2L$ in which L is a suitable leaving group, such as a carboxyl group or carbonylalkoxy group, as described in published UK Patent Application No. 2182328. The preparation of suitable phthalic anhydride derivatives is also described therein.

Compounds where X is sulphur may be obtained by reaction of the corresponding carbonyl analogue with phosphorus pentasulphide.

The compounds of general formula II have been found to show interesting activity as herbicides, in particular in respect of their behavior in selectively combating weeds in cereal crops such as wheat and rice. Accordingly, the invention further provides a herbicidal composition comprising a compound of formula II as defined above in association with at least one carrier, and a method of making such a composition which comprises bringing a compound of formula II into association with at least one carrier.

The invention also provides the use of such a compound or composition according to the invention as a herbicide. Further, in accordance with the invention there is provided a method of combating undesired plant growth at a locus by treating the locus with a compound or composition according to the invention. Application to the locus may be pre-emergence or post-emergence. The dosage of active ingredient used may, for example, be from 0.01 to 10 kg/ha, preferably 0.01 to 4 kg/ha. A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulphate; ammonium sulphate; synthetic hydrated silicon oxides and synthetic calcium or aluminum silicates; elements, for example carbon and sulphur; natural and synthetic resins, for example coumarone resins, polyvinyl chloride, and styrene polymers and copolymers; solid polychlorophenols; bitumen; waxes; and solid fertilizers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilizers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

The invention is illustrated by the following Examples.

N.M.R. spectral data was obtained by QE 300 Spectrometer at 300 mHz using $CDCl_3$ as solvent.

EXAMPLE 1

5-(2'-Chloro-4'-trifluoromethylphenoxy)-3-ethyl-3-ethynyl phthalide

To dry, degreased magnesium metal turnings (3.0 g), dry tetrahydrofuran (240 ml) was added and dry nitrogen bubbled in. Bromoethane (13.2 g) was added dropwise with stirring and maintenance of the temperature between 15° and 20° C. during the formation of the Grignard reagent. After all the magnesium had reacted (about 1 hour), the nitrogen was replaced by dry acetylene, which was bubbled in at 15° C. until no further ethane was evolved. 5-(2'-chloro-4'-trifluoromethylphenoxy)-3-ethyl-3-hydroxyphthalide (6.0 g) in dry tetrahydrofuran (100 ml) was added dropwise at 15° C. over 1 hour whilst acetylene was bubbled in. After addition was complete, the reaction mixture was stirred at 15° C. for 1 hour and then poured onto 1 kg ice and acidified with concentrated hydrochloric acid. The resulting mixture was extracted with methylene chloride, washed with water, dried using sodium sulphate and chromatographically purified on silica using methylene chloride as eluant. The title compound was collected as the first fraction.

| | | | |
|---|---|---|---|
| Yield 5.6 g. m.p. 57-59° C. | | | |
| Analysis: | Calculated: | 59.9% C; | 3.15% H |
| | Found: | 59.7% C; | 3.5% H |
| NMR results: | 7.85 doublet (1H); 7.8 doublet (1H); | | |
| | 7.6 doublet of doublets (1H); | | |
| | 7.2 doublet (1H); 7.1 doublet | | |
| | of doublets (1H); 7.05 doublet (1H) | | |
| | 2.7 singlet (1H); 2.2 sextet (1H); | | |
| | 2.0 sextet (1H); 1.05 triplet (3H) | | |

EXAMPLE 2

5-(2'Chloro-4'-trifluoromethylphenoxy)-3-ethyl-3-vinyl phthalide

To a 1M solution of vinyl magnesium bromide in tetrahydrofuran (46 ml) was added dropwise at 25° C. a solution of 5-(2'-chloro-4'trifluoromethylphenoxy)-3-ethyl-3-hydroxy- phthalide (2.3 g) in dry tetrahydrofuran (25 ml). After the addition was complete, the solution was stirred for 1 hour and poured into a mixture of ice and concentrated hydrochloric acid. The mixture was stirred for one hour, extracted with methylene chloride, washed with water and dried with sodium sulphate. Chromatography on silica with methylene chloride as eluant yielded a pale orange oil later obtained as colorless crystals (mp. 77°-79° C.).

| | | | |
|---|---|---|---|
| Analysis: | Calculated: | 59.6% C; | 3.7% H |
| | Found: | 58.5% C; | 3.7% H |
| NMR results: | 7.85 doublet (1H); 7.8 doublet (1H); | | |
| | 7.55 doublet of doublets (1H); 7.2 | | |
| | doublet (1H); | | |
| | 7.05 doublet of doublets (1H); 6.9 | | |
| | doublet (1H); | | |
| | 6.05-5.2 multiplet (3H); 2.1 sextet | | |
| | (1H); | | |
| | 1.95 sextet (1H); 0.8 triplet (3H) | | |

EXAMPLE 3

5-(2'Chloro-4'-trifluoromethylphenoxy)-3-methyl-3-ethynyl phthalide

Using as starting material 5-(2'-chloro-4'-trifluoromethylphenoxy)-3-methyl-3-hydroxyphthalide the above compound was prepared using the method of Example 1.

| | | | |
|---|---|---|---|
| Analysis: | Calculated: | 58.9% C; | 2.7% H |
| | Found: | 58.7% C; | 2.9% H |
| NMR analysis: | 7.88-7.04 multiplet (6H); 2.68 singlet | | |
| | (1H); | | |
| | 1.9 singlet (3H) | | |

EXAMPLE 4

5-(2'-Chloro-4'-trifluoromethylphenoxy)-3-methyl-3-vinyl phthalide

Using as starting material 5-(2'-chloro-4'-trifluoromethylphenoxy)-3-methyl-3-hydroxyphthalide the above compound was prepared as colorless crystals (mp 71°-73°) using the method of Example 2.

| | | | |
|---|---|---|---|
| Analysis: | Calculated: | 58.6% C; | 3.3% H |
| | Found: | 58.5% C; | 3.3% H |
| NMR analysis: | 7.88-6.86 multiplet (6H); 6.08-5.96 | | |
| | doublet of | | |
| | doublets (1H); 5.46-5.18 doublet of | | |
| | doublets (2H); 1.72 singlet (3H) | | |

EXAMPLE 5

Herbicidal Activity

To evaluate their herbicidal activity, compounds according to the invention were tested using as a representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant specied mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 900 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0-9 scale. A rating 0 indicates growth as untreated control, a rating 9 indicates death. An increase of 1 unit on the linear scale approximates to a 10% increase in the level of effect.

The results of the tests are set out in Table 1 below, in which the compounds are identified by reference to the preceding examples.

to 0.2% of the alkylphenol/ethylene oxide wetting agent, Triton X155 (trade mark) and applied as single dose foliar sprays in a total volume of 600 liters/hectare. Application was at 4 different dosage levels 0.3, 0.1, 0.03 and 0.01 kg/ha designed to produce a range of responses. At least two replicate pots were used for each treatment. Untreated seedling plants were used as controls.

Phytotoxicity compared with the untreated control was assessed visually approximately 12 days after treatment using the standard 0-9 scale, 0 indicating no effect and 9 indicating death.

The results were subjected to a standard probit analysis by computer to calculate the dosage of each compound in g/ha required to kill 50% of the weed species and to produce 50% level of effect on the crop species. These dosages are referred to as the GID$_{50}$ value.

The GID$_{50}$ values comparing the compounds of Examples 1 to 4 with A are set out below in Table 2. These GID$_{50}$ values were then used to calculate the selectivity factors in wheat by dividing the GID$_{50}$ value of the compounds in wheat by their GID$_{50}$ value in each weed species. The results are set out in Table 3. (NB. Numbers greater than 1 indicate selectivity between crop and weed and the larger the number the greater the selectivity).

Table 4 compares the selectivity factors for Examples 1 to 4 with that of A showing the increased mean selectivity for each Examples 1 to 4 compared with A.

TABLE 2

| | GID 50 values in g/ha for all compounds | | | | |
|---|---|---|---|---|---|
| Species | Compound A | Ex. 4 | Ex. 3 | Ex. 2 | Ex. 1 |
| WH | 111 | 37 | 14 | 108 | 31 |
| FP | 14 | 6 | 3 | 30 | 5 |
| SW | 12 | 8 | 1 | 63 | 7 |

TABLE 1

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 4 | 0 | 4 | 5 | 0 | 4 | 6 | 0 | 5 | 8 | 6 | 9 | 9 | 9 | 9 | 9 | 8 | 5 | 4 | 9 | 8 | 9 | 9 | 9 | 6 |
| | | | | | | | | | 1 | 6 | 3 | 9 | 9 | 9 | 9 | 9 | 8 | 3 | 2 | 9 | 7 | 9 | 9 | 8 | 4 |
| 2 | 4 | 0 | 4 | 4 | 3 | 2 | 6 | 0 | 5 | 7 | 5 | 9 | 9 | 9 | 9 | 9 | 8 | 4 | 2 | 9 | 7 | 9 | 9 | 9 | 4 |
| | | | | | | | | | 1 | 6 | 2 | 9 | 9 | 9 | 9 | 9 | 8 | 2 | 1 | 8 | 6 | 8 | 9 | 8 | 0 |
| 3 | 5 | 3 | 8 | 8 | 8 | 8 | 9 | 7 | 5 | 8 | 8 | 9 | 9 | 9 | 9 | 9 | 9 | 5 | 5 | 9 | 9 | 9 | 9 | 9 | 7 |
| | | | | | | | | | 1 | 6 | 5 | 9 | 9 | 9 | 9 | 9 | 9 | 3 | 3 | 9 | 7 | 9 | 9 | 9 | 4 |
| 4 | 4 | 2 | 7 | 7 | 8 | 7 | 8 | 4 | 5 | 8 | 6 | 9 | 9 | 9 | 9 | 9 | 9 | 7 | 5 | 9 | 8 | 8 | 9 | 9 | 7 |
| | | | | | | | | | 1 | 6 | 6 | 9 | 9 | 9 | 9 | 9 | 8 | 2 | 3 | 7 | 5 | 7 | 8 | 8 | 4 |

EXAMPLE 6

Herbicidal Activity

Further biological evaluations were carried with the compounds of Examples 1 to 4, which compared their properties with those of 5-(2'-chloro-4'-trifluoromethylphenoxy)phthalide, (hereinafter designated as "A") specifically described as Example 1 of EP-A-145078.

The tests conducted were spray tests, in which seedling plants of a range of species were sprayed with the test compounds. The test plant species were wheat (WH), chickweed (ST), mayweed (MS), speedwell (SW), field pansy (FP), cleavers (GG), dead nettle (DN), poppy (PO), redshank (RS), hedge bindweed (SE) and oil-seed rape (RA). The plants were at the stage of 1-3 true leaves.

The soil used in the test was a prepared horticultural loam.

The compounds were tested as technical materials and formulated in a 1:1 acetone:water mix containing up

| | | | | | |
|---|---|---|---|---|---|
| GG | 42 | 10 | 13 | 44 | 7 |
| MS | 279 | 5 | 3 | 19 | 8 |
| ST | 149 | 29 | 2 | 18 | 5 |
| SE | 591 | 37 | 10 | 175 | 18 |
| DN | 29 | 10 | 3 | 23 | 6 |
| PO | 191 | 10 | 6 | 26 | 9 |
| RS | 9 | 5 | 2 | 23 | 9 |
| RA | 427 | 8 | 2 | 30 | 6 |

TABLE 3

| | Selectivity factors obtained for wheat using GID 50 values | | | | |
|---|---|---|---|---|---|
| Species | Compound A | Ex. 4 | Ex. 3 | Ex. 2 | Ex. 1 |
| FP | 7.9 | 6.2 | 4.7 | 3.6 | 6.2 |
| SW | 9.3 | 4.6 | 14.0 | 1.7 | 4.4 |
| GG | 2.6 | 3.7 | 1.1 | 2.5 | 4.4 |
| MS | 0.4 | 7.4 | 4.7 | 5.7 | 3.9 |
| ST | 0.7 | 1.3 | 7.0 | 6.0 | 6.2 |
| SE | 0.2 | 1.0 | 1.4 | 0.6 | 1.7 |
| DN | 3.8 | 3.7 | 4.7 | 4.7 | 5.2 |

TABLE 3-continued standard 0-9 scale (0=no effect; 9=dead). The results are given in Table 5.

TABLE 5

| COMPOUND OF EXAMPLE NO. | DOSAGE g/ha | EC PE | EC PO | CD PE | CD PO | MV PE | MV PO | BLW PE | BLW PO | CS PE | CS PO | SP PE | SP PO | RICE PT | RICE TR |
|---|---|---|---|---|---|---|---|---|---|---|---|---|---|---|---|
| 1 | 500 | 9 | 8.5 | 9 | 9 | 9 | 9 | 9 | 9 | 9 | 8 | 9 | 7 | 3 | 2 |
| 1 | 250 | 9 | 8 | 9 | 9 | 9 | 9 | 9 | 9 | 9 | 7 | 8 | 5 | 2 | 2 |
| 1 | 125 | 9 | 8 | 9 | 9 | 9 | 9 | 9 | 9 | 9 | 6 | 7 | 4 | 1 | 2 |
| 1 | 62.5 | 9 | 6 | 9 | 9 | 9 | 9 | 9 | 9 | 9 | 6 | 5 | 4 | 0.5 | 0.5 |
| 1 | 31.25 | 8.5 | 4 | 9 | 9 | 9 | 9 | 9 | 9 | 9 | 5 | 4 | 2 | 0.5 | 0.5 |
| 4 | 500 | 9 | 8.5 | 9 | 9 | 9 | 9 | 9 | 9 | 9 | 8 | 8 | 6 | 3 | 2 |
| 4 | 250 | 9 | 8.5 | 9 | 9 | 9 | 9 | 9 | 9 | 9 | 7 | 7 | 5 | 2 | 2 |
| 4 | 125 | 9 | 7 | 9 | 9 | 9 | 9 | 9 | 9 | 9 | 7 | 6 | 4 | 2 | 1 |
| 4 | 62.5 | 8.5 | 5 | 9 | 9 | 9 | 9 | 9 | 9 | 8 | 7 | 4 | 3 | 1 | 0.5 |
| 4 | 31.25 | 8.5 | 1 | 9 | 9 | 9 | 9 | 9 | 9 | 5 | 6 | 3 | 1 | 0.5 | 0.5 |

Selectivity factors obtained for wheat using GID 50 values

| Species | Compound A | Ex. 4 | Ex. 3 | Ex. 2 | Ex. 1 |
|---|---|---|---|---|---|
| PO | 0.6 | 3.7 | 2.3 | 4.2 | 3.4 |
| RS | 12.3 | 7.4 | 7.0 | 4.7 | 3.4 |
| RA | 0.3 | 4.6 | 7.0 | 3.6 | 5.2 |

TABLE 4

Selectivity factors standardised to Compound A

| Species | Compound A | Ex. 4 | Ex. 3 | Ex. 2 | Ex. 1 |
|---|---|---|---|---|---|
| FP | 1.0 | 0.8 | 0.6 | 0.5 | 0.8 |
| SW | 1.0 | 0.5 | 1.5 | 0.2 | 0.5 |
| GG | 1.0 | 1.4 | 0.4 | 1.0 | 1.7 |
| MS | 1.0 | 18.5 | 11.8 | 14.3 | 9.8 |
| ST | 1.0 | 1.9 | 10.0 | 8.6 | 8.9 |
| SE | 1.0 | 5.0 | 7.0 | 3.0 | 8.5 |
| DN | 1.0 | 1.0 | 1.2 | 1.2 | 1.4 |
| PO | 1.0 | 6.2 | 3.8 | 7.0 | 5.7 |
| RS | 1.0 | 0.6 | 0.6 | 0.4 | 0.3 |
| RA | 1.0 | 15.3 | 23.3 | 12.0 | 17.3 |
| MEAN | 1.0 | 5.1 | 6.0 | 4.8 | 5.5 |

EXAMPLE 7

Herbicidal Activity

To further evaluate their herbicidal activity, the compounds of Examples 1 and 4 were tested to demonstrate their selectivity in paddy rice (Oryza Sativa) using as a representative range of plants: Echinochloa crus-galli (EC), Cyperus difformis (CD), Monochoria vaginalis (MV), Scirpus hotarui (SM), Cyperus serotinus (CS), Sagittaria pygmaea (SP), and a mixture of broadleaved weeds (BLW).

The soil used for the tests was collected from Japanese paddy fields and used in small plot containers without drainage holes. Water depth was 10-20 mm.

Rice plants at the two leaf stage were transplanted as three separate clumps each containing three plants in containers similar to those used for the weed species.

The compounds were dissolved in a minimum amount of acetone, diluted with water and applied evenly to the paddy water with a pipette. Application was at 5 different dosage levels, i.e. 500, 250, 125, 62.5 and 31.25 g/ha.

Application was pre-emergence (PE) (after germination, before emergence) or post-emergence (PO) (after growth to 1 to 2 leaves). Application to rice was pre-transplanting (PT) or after transplanting (TR). Phytotoxicity was assessed after 21 days visually using the

We claim:

1. A phenoxy phthalide derivative of the general formula II

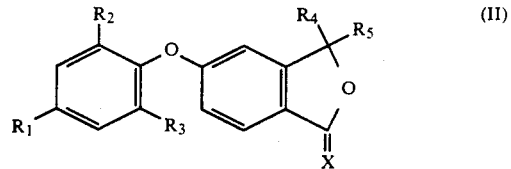

wherein $R_1$ represents a hydrogen or halogen atom or a $C_{1-4}$ alkyl or a $C_{1-4}$ haloalkyl group; $R_2$ and $R_3$, which may be the same or different, each independently represents a hydrogen or halogen atom or a $C_{1-4}$ alkyl, a $C_{1-4}$ haloalkyl, nitro or cyano group; $R_4$ represents a $C_{1-5}$ alkyl group; $R_5$ represents a $C_{2-5}$ alkenyl or alkynyl group; and X represents an oxygen or sulphur atom.

2. A compound as claimed in claim 1 wherein $R_1$ represents a trifluoromethyl group; $R_2$ represents a halogen atom; and $R_3$ represents a hydrogen atom.

3. A compound as claimed in claim 1 or 2, wherein X is O.

4. A compound as claimed in claim 1 or 2, wherein $R_4$ represents a methyl or ethyl group.

5. A compound as claimed in claims 1 or 2, wherein $R_5$ represents a vinyl group or an ethynyl group.

6. The compound of claim 1 which is 5-(2'-chloro-4-'-trifluoromethylphenoxy)-3-ethyl-3-ethynyl phthalide.

7. The compound of claim 1 which is 5-(2'-chloro-4'-trifluoromethylphenoxy)-3-methyl-3-vinyl phthalide.

8. A compound as claimed in claim 4 wherein $R_4$ represents methyl.

9. A compound as claimed in claim 5 wherein $R_4$ represents methyl.

10. A compound as claimed in claim 5 wherein $R_5$ represents ethynyl.

11. A compound as claimed in claim 1 which is 5-(2'-chloro-4'-trifluoromethylphenoxy)-3-ethyl-3-vinyl phthalide.

12. A compound as claimed in claim 1 which is 5-(2'-chloro-4'-trifluoromethylphenoxy)-3-methyl-3-ethynyl phthalide.

13. A herbicidal composition, which comprises an effective amount of a compound as claimed in claim 1, together with a carrier.

* * * * *